United States Patent
Wakito et al.

(10) Patent No.: US 12,011,145 B2
(45) Date of Patent: Jun. 18, 2024

(54) ENDOSCOPE DISTAL END STRUCTURE AND ENDOSCOPE

(71) Applicant: OLYMPUS CORPORATION, Tokyo (JP)

(72) Inventors: Sumio Wakito, Hachioji (JP); Masayoshi Miura, Fuchu (JP); Satoru Adachi, Tsuchiura (JP); Hiroyuki Motohara, Hachioji (JP); Shigeru Hosokai, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 278 days.

(21) Appl. No.: 17/347,770

(22) Filed: Jun. 15, 2021

(65) Prior Publication Data
US 2021/0307590 A1 Oct. 7, 2021

Related U.S. Application Data (63) Continuation of application No. PCT/JP2018/046648, filed on Dec. 18, 2018.

(51) Int. Cl.
*A61B 1/00* (2006.01)
*A61B 1/06* (2006.01)

(52) U.S. Cl.
CPC ...... *A61B 1/00096* (2013.01); *A61B 1/00114* (2013.01); *A61B 1/0684* (2013.01)

(58) Field of Classification Search
CPC .............. A61B 1/0008; A61B 1/00096; A61B 1/00101; A61B 1/00105; A61B 1/00114; A61B 1/051; A61B 1/053; A61B 1/0684
See application file for complete search history.

(56) References Cited

U.S. PATENT DOCUMENTS

| | | | | |
|---|---|---|---|---|
| 5,040,069 | A | * | 8/1991 | Matsumoto ............ H04N 23/54 348/340 |
| 2013/0050457 | A1 | * | 2/2013 | Murayama ......... G02B 23/2484 348/75 |

(Continued)

FOREIGN PATENT DOCUMENTS

| JP | H10248803 | A | * | 9/1998 |
| JP | H11305146 | A | * | 11/1999 |

(Continued)

OTHER PUBLICATIONS

International Search Report dated Mar. 26, 2019 received in PCT/JP2018/046648.

*Primary Examiner* — Aaron B Fairchild
(74) *Attorney, Agent, or Firm* — Scully, Scott, Murphy & Presser, P.C.

(57) ABSTRACT

An endoscope distal end structure includes: an imager, a distal end frame that is a three-dimensional molded interconnect device including a housing portion and a cable connecting portion, the cable connecting portion including a cable connection electrode, the housing portion being formed by cutting out at least a part of an outer peripheral portion of the distal end frame, the housing portion having a bottom surface on which connection terminals are formed, and a first side surface and a second side surface which are continuous to each other and on which a ground pattern is formed, a through hole having electrical conductivity, the through hole penetrating from the bottom surface to the cable connecting portion, and an electrical conductive pattern connecting a cable connection electrode and the ground pattern, the electrical conductive pattern being arranged on a side surface of the distal end frame.

13 Claims, 7 Drawing Sheets

(56) References Cited

U.S. PATENT DOCUMENTS

| | | | |
|---|---|---|---|
| 2017/0127915 A1* | 5/2017 | Viebach | A61B 1/0057 |
| 2017/0127921 A1* | 5/2017 | Motohara | H04N 23/57 |
| 2019/0133423 A1* | 5/2019 | Birnkrant | A61B 1/04 |

FOREIGN PATENT DOCUMENTS

| | | | |
|---|---|---|---|
| JP | 2017-023234 A | | 2/2017 |
| JP | 2017113417 A | * | 6/2017 |
| JP | 2017-209278 A | | 11/2017 |
| WO | 2012/124526 A1 | | 9/2012 |

* cited by examiner

ENDOSCOPE DISTAL END STRUCTURE AND ENDOSCOPE

CROSS-REFERENCE TO RELATED APPLICATION

This application is a continuation of International Application No. PCT/JP2018/046648, filed on Dec. 18, 2018, the entire contents of which are incorporated herein by reference.

BACKGROUND

1. Technical Field

The present disclosure relates to an endoscope distal end structure provided at a distal end of an insertion portion of an endoscope to be inserted into a subject, and an endoscope.

2. Related Art

In the related art, an endoscope has a configuration with a flexible and elongated insertion portion including, at its distal end, an imager, and when the insertion portion is inserted into a subject such as a patient, image data of the inside of the subject is acquired by the imager at the distal end portion so as to be transmitted to an external information processing device by a signal cable.

In recent years, there has been proposed an endoscope in which the distal end of an insertion portion uses resin instead of metal as a constituent member. The use of a resin member, however, requires a mechanism for preventing destruction of an image sensor in a case where static electricity is applied.

As a proposed technique for preventing leakage current and static electricity from flowing through the image sensor, there is an endoscope having a circuit pattern provided on an inner peripheral surface of a fixing hole to which a lens frame of a distal end frame is fixed so as to connect the endoscope to a curved tube being an electrical conductive member (refer to JP 2017-209278 A, for example).

SUMMARY

In some embodiments, an endoscope distal end structure includes: an imager configured to capture an object image, a distal end frame that is a three-dimensional molded interconnect device in which a housing portion is provided on a distal end side and a cable connecting portion is provided on a proximal end side, the housing portion being configured to house the imager, the cable connecting portion including a cable connection electrode to which a cable is connected, the housing portion being formed by cutting out at least a part of an outer peripheral portion of the distal end frame, the housing portion having a bottom surface on which connection terminals connected to terminals of the imager are formed, and a first side surface and a second side surface which are continuous to each other and on which a ground pattern is formed, a through hole having electrical conductivity, the through hole penetrating from the bottom surface to the cable connecting portion on an opposite side of the bottom surface, and an electrical conductive pattern connecting a cable connection electrode and the ground pattern, the electrical conductive pattern being arranged on a side surface of the distal end frame, the cable connection electrode being connected to a ground terminal among the connection terminals.

In some embodiments, an endoscope includes the endoscope distal end structure.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, an endoscope system including an endoscope distal end structure will be described according to embodiments of the disclosure (hereinafter, referred to as "embodiment (s)"). The disclosure is not limited by the present embodiment. In the drawings, same reference signs are attached to the same portions. Furthermore, it needs to be kept in mind that the drawings are schematic, and the relationship between the thickness and the width of individual members, and the ratios and angles between the members are different from an actual case. Furthermore, dimensions, ratios, and angles can be mutually different in individual drawings.

Figure 1:
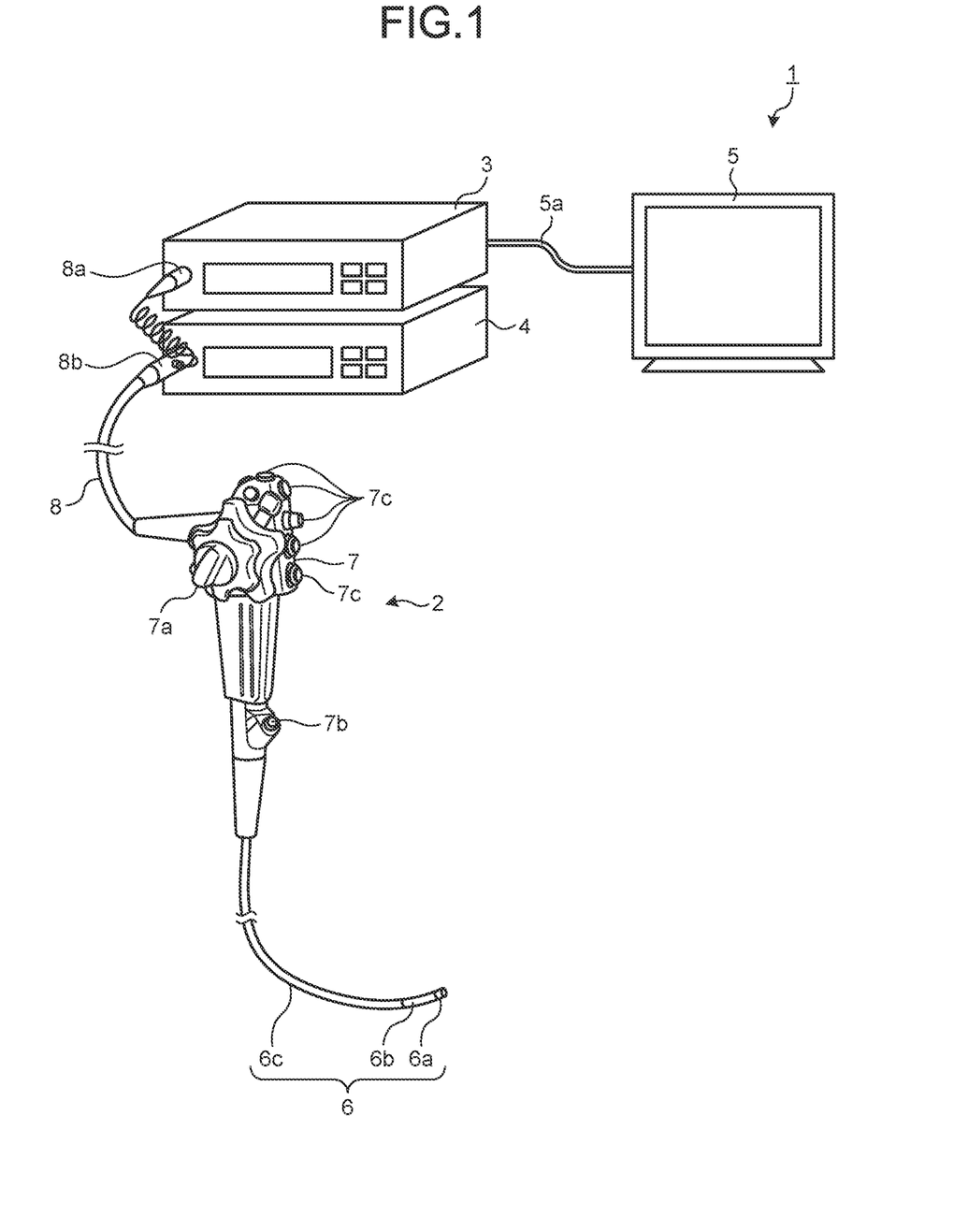
FIG. 1 is a block diagram schematically illustrating an overall configuration of an endoscope system according to an embodiment of the disclosure.

FIG. 1 is a view schematically illustrating an overall configuration of an endoscope system 1 according to a first embodiment of the disclosure. As illustrated in FIG. 1, an endoscope system 1 according to the first embodiment includes: an endoscope 2 that is introduced into a subject and captures an image inside the body of the subject and generates an image signal of the interior of the subject; an information processing device 3 that performs predetermined image processing on the image signal captured by the endoscope 2 and controls individual portions of the endoscope system 1; a light source device 4 that generates illumination light for the endoscope 2; and a display device 5 that displays an image of the image signal after undergoing image processing by the information processing device 3.

The endoscope 2 includes: an insertion portion 6 that is inserted into the subject; an operating unit 7 arranged on a proximal end side of the insertion portion 6 and gripped by an operator; and a universal cord 8 that has flexibility and extends from the operating unit 7.

The insertion portion 6 is formed with a light guide cable, an electric cable, an optical fiber, or the like. The insertion portion 6 includes: a distal end portion 6a that incorporates an imager described below; a bending portion 6b which is a bendable portion formed with a plurality of bending pieces; and a flexible tube portion 6c which is flexible and provided on a proximal end side of the bending portion 6b. The distal end portion 6a is provided with an aperture that provides a passage for devices such as a light guide cable for illuminating the inside of the subject, an imager for imaging the inside of the subject, and a treatment tool channel.

The operating unit 7 includes: a bending knob 7a used to bend the bending portion 6b in up-down and left-right directions; a treatment tool insertion portion 7b through which treatment tools such as biological forceps and a laser knife are inserted into the body cavity of the subject; and a plurality of switch portions 7c used to operate peripheral devices such as the information processing device 3, the light source device 4, an air feeding device, a water feeding device, and a gas feeding device. A treatment tool inserted from the treatment tool insertion portion 7b passes through the treatment tool channel provided inside, and comes out from the aperture of the distal end of the insertion portion 6.

The universal cord 8 is formed by using a light guide cable, an electric cable, or the like. The universal cord 8 is branched at a proximal end. One end of the branched section is a connector 8a, and the other proximal end is a connector 8b. The connector 8a is removably attached to the connector of the information processing device 3. The connector 8b is removably attached to the light source device 4. The universal cord 8 transmits illumination light emitted from the light source device 4 to the distal end portion 6a via the connector 8b and the light guide cable. Moreover, the universal cord 8 transmits an image signal captured by an imager to be described below to the information processing device 3 via the cable and the connector 8a.

The information processing device 3 performs predetermined image processing on the image signal output from the connector 8a, while controlling the whole endoscope system 1.

The light source device 4 is constituted with a light source that emits light, a condenser lens, or the like. Under the control of the information processing device 3, the light source device 4 emits light from the light source and supplies the light to the endoscope 2 connected via the connector 8b and the light guide cable of the universal cord 8, as illumination light supplied to the interior of a subject as an object.

The display device 5 includes a display using liquid crystal or organic electro luminescence (EL). The display device 5 displays, via a video cable 5a, various types of information including an image that has undergone predetermined image processing performed by the information processing device 3. With this configuration, the operator can observe a desired position inside the subject and determine conditions by operating the endoscope 2 while viewing an image (in-vivo image) displayed by the display device 5.

Figure 2:
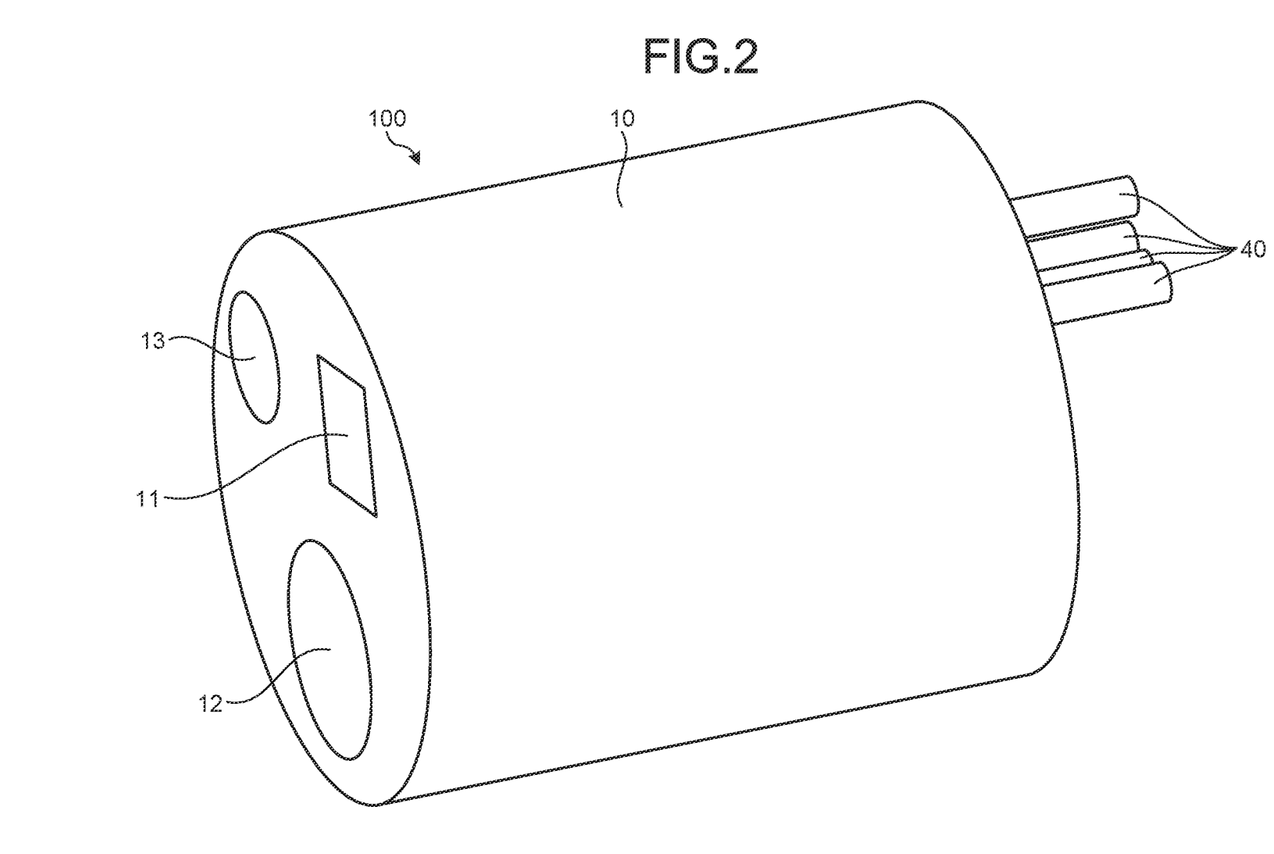
FIG. 2 is a perspective view of an endoscope distal end structure arranged at a distal end portion of the endoscope illustrated in FIG. 1.
Figure 3A:
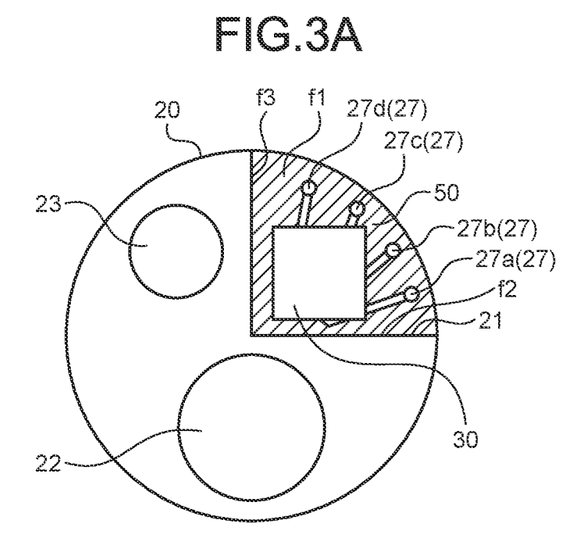
FIG. 3A is a front view of a state in which an outer frame is removed from the endoscope distal end structure of FIG. 2.
Figure 3B:
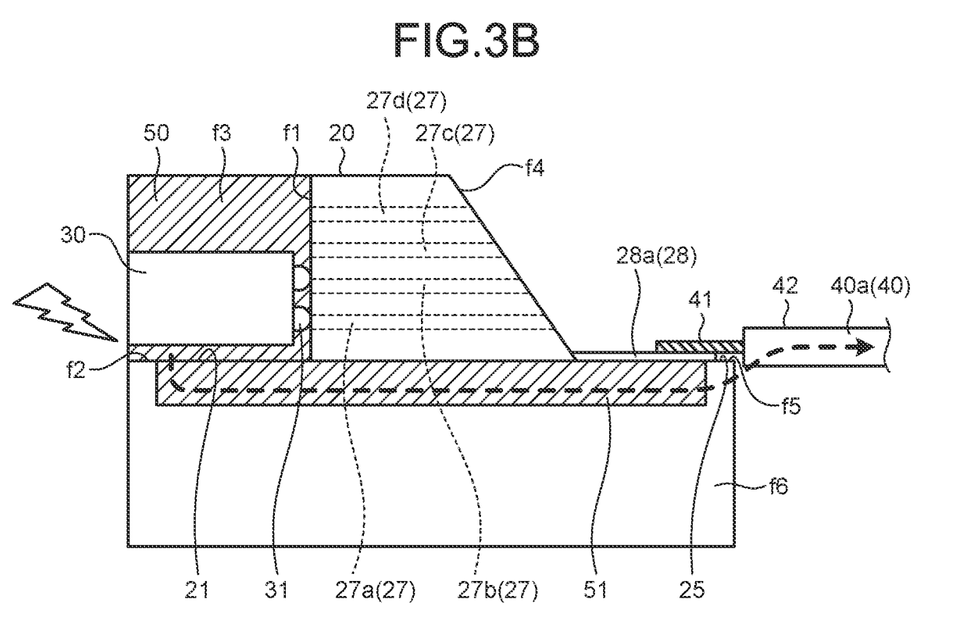
FIG. 3B is a side view of a state in which an outer frame is removed from the endoscope distal end structure of FIG. 2.
Figure 3C:
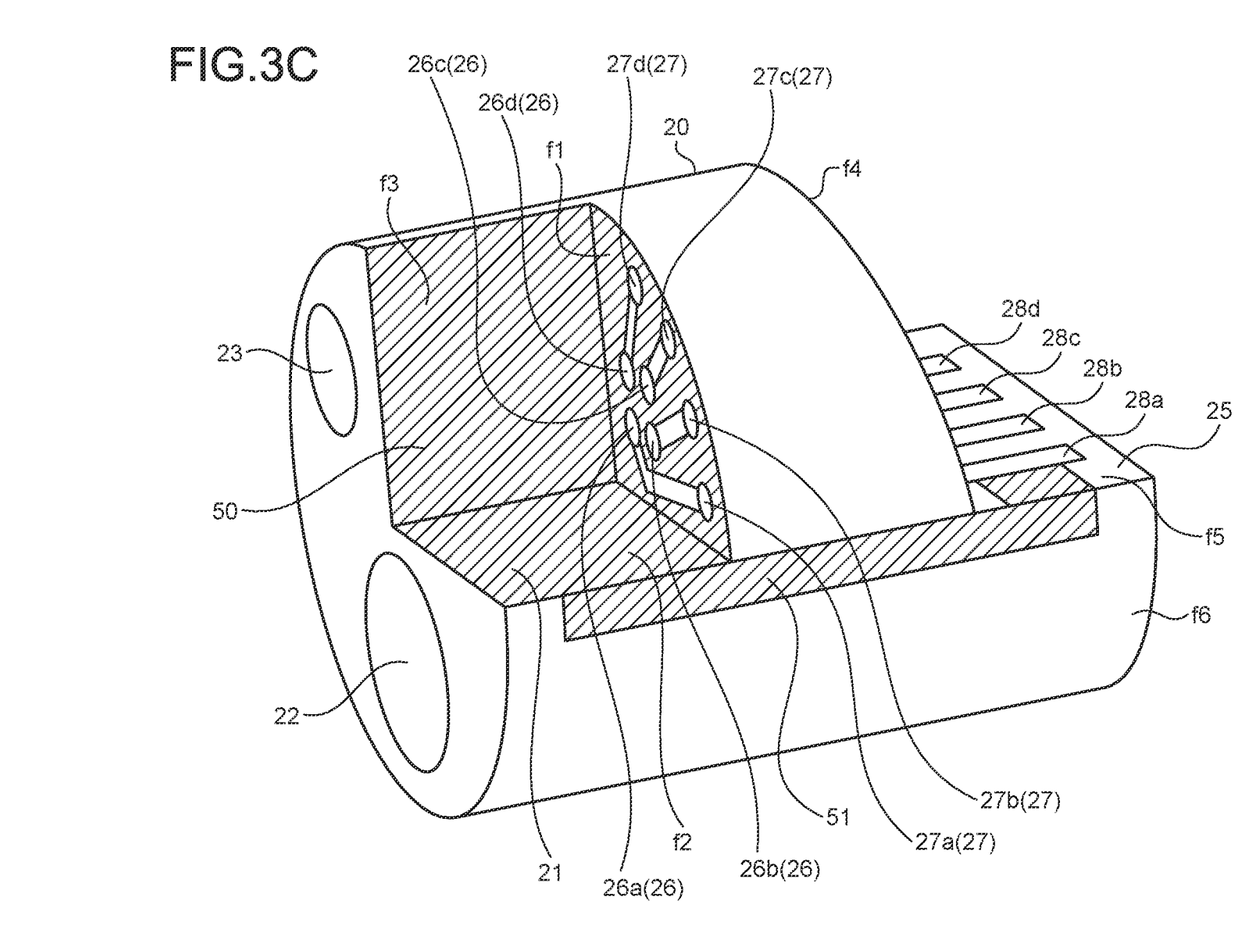
FIG. 3C is a perspective view of a distal end frame used in the endoscope distal end structure of FIG. 2.
Figure 3D:
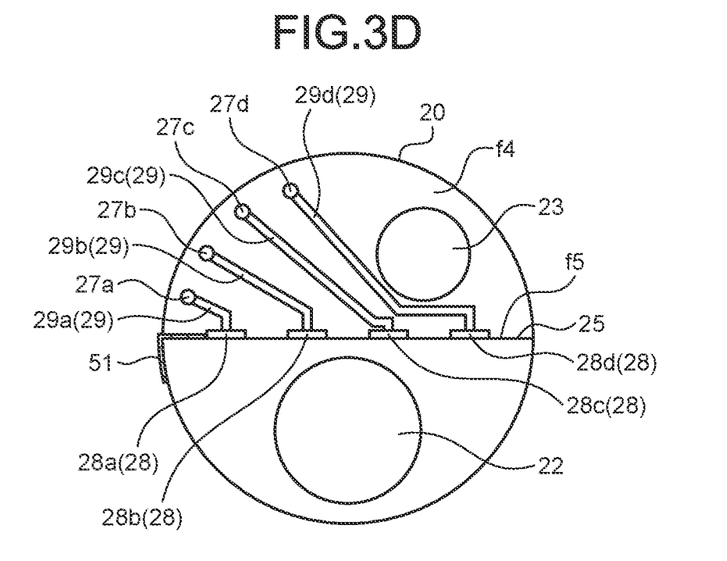
FIG. 3D is a rear view of a distal end frame used in the endoscope distal end structure of FIG. 2.
Figure 3E:
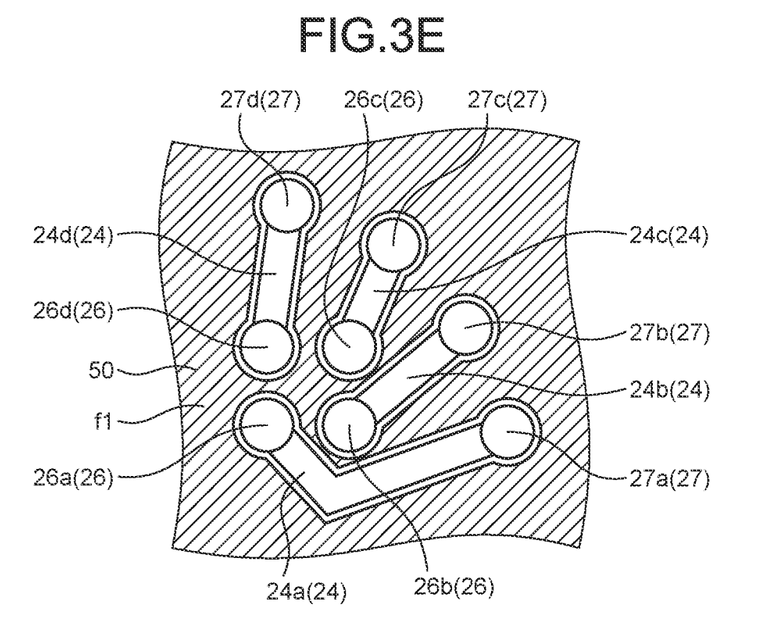
FIG. 3E is a bottom view of a housing portion of the distal end frame used in the endoscope distal end structure of FIG. 2.
Figure 3F:
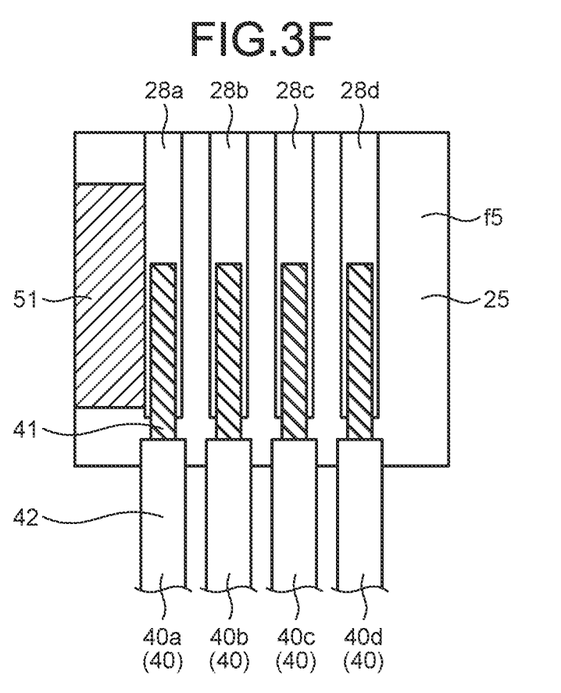
FIG. 3F is a view illustrating a cable connecting portion of a distal end frame used in the endoscope distal end structure of FIG. 2.

Next, an endoscope distal end structure 100 used in the endoscope system 1 will be described in detail. FIG. 2 is a perspective view of the endoscope distal end structure 100 disposed at a distal end portion of the endoscope 2 illustrated in FIG. 1. FIG. 3A is a front view of a state in which an outer frame is removed from the endoscope distal end structure of FIG. 2. FIG. 3B is a side view of a state in which the outer frame is removed from the endoscope distal end structure of FIG. 2. FIG. 3C is a perspective view of a distal end frame used for the endoscope distal end structure of FIG. 2. FIG. 3D is a rear view of a distal end frame used for the endoscope distal end structure of FIG. 2. FIG. 3E is a bottom view of a housing portion of the distal end frame used for the endoscope distal end structure of FIG. 2. FIG. 3F is a view illustrating a cable connecting portion of the distal end frame used for the endoscope distal end structure of FIG. 2. FIGS. 2 and 3B omit illustration of the light guide and the channel. In the present specification, the distal end portion 6a side of the endoscope 2 is referred to as a distal end side, and the side from which a cable 40 extends is referred to as a proximal end side.

The endoscope distal end structure 100 includes: an imager 30 that captures an object image; a distal end frame 20 that is a three-dimensional molded interconnect device in which a housing portion 21 that stores the imager 30 is provided on a distal end side, and a cable connecting portion 25 having a cable connection electrode 28 to which a cable 40 is connected is provided on a proximal end side; and an outer frame 10 formed of a material having no electrical conductivity, the outer frame 10 being configured to cover the distal end frame 20.

The imager 30 includes: an optical unit (not illustrated) that forms an image of an object; and an image sensor (not illustrated) that photoelectrically converts the object image formed by the optical unit to generate an image signal. Side surfaces of the optical unit and the image sensor are held by a frame member or coated with a coating material that prevents light transmission. The image sensor includes a CCD, a CMOS, or the like, and the light receiving portion is covered with a glass cover slide.

The distal end frame 20 is a molded interconnect device (MID) including three-dimensional wiring formed by injection molding. In the present embodiment, by using the MID as the distal end frame 20, it is possible to achieve manufacture easily and inexpensively even with a complicated structure. By using the molded interconnect device as the distal end frame 20, it is possible to manufacture the endoscope distal end structure 100 easily and inexpensively. Incidentally, the distal end frame 20 may be obtained by molding by cutting, with formation of three-dimensional wiring.

The distal end frame 20 includes: a housing portion 21 that houses the imager 30; a channel insertion hole 22 that allows insertion of the channel tube; a light guide insertion hole 23 that allows insertion of the light guide; and a cable connecting portion 25 that connects the cable 40. The channel insertion hole 22 and the light guide insertion hole 23 are through holes penetrating from the distal end side to the proximal end side of the distal end frame 20, and are arranged in parallel to an optical axis direction of the imager 30.

The distal end frame 20 has a substantially columnar shape obtained by cutting out the housing portion 21 and the cable connecting portion 25 from a columnar shape. The distal end frame 20 of the present embodiment has a columnar outer shape, but is not limited to this shape. As the outer shape of the distal end frame 20, it is possible to adopt shape applicable to the endoscope distal end structure, such as a polygonal columnar shape, a columnar shape having an outer shape of the bottom surface obtained by cutting out a part of a circle, a columnar shape having an outer shape of the bottom surface partially protruding from the circular shape, or the like.

The housing portion 21 is obtained by cutting out a part of an outer peripheral portion of the distal end frame 20 on the distal end side. The housing portion 21 has a bottom surface f1 which is orthogonal to the optical axis of the imager 30 and on which a connection terminal 26 connected to a terminal of the image sensor is formed, and a first side surface f2 and a second side surface f3 which are continuous to each other in parallel to the optical axis. There is provided a ground pattern 50 on the entire surfaces of the first side surface f2 and the second side surface f3, and around the connection terminal 26, a through hole 27, and a wiring pattern 24 connecting the connection terminal 26 and the through hole 27 on the bottom surface f1. Although the first side surface f2 and the second side surface f3 are orthogonal to each other, a corner portion between the first side surface f2 and the second side surface f3 may be chamfered. A connection land (not illustrated) of the imager 30 is electrically and mechanically connected to the connection terminals 26 by a bump 31 formed of solder or the like. The connection terminals 26 include a ground terminal 26a, a communication terminal 26b provided also for a clock necessary for driving the imager 30, a signal output terminal 26c, and a power supply terminal 26d. Note that, although not illustrated in FIGS. 3A and 3C, a gap between the imager 30 and the housing portion 21 (connection portion between the imager 30 and the connection terminal 26) and the wiring pattern 24 and an upper portion of the through hole 27 on the f1 surface side are covered with an insulating material such as an underfill material.

The ground terminal 26a is connected to an electrical conductive through hole 27a by a wiring pattern 24a; the communication terminal 26b is connected to an electrical conductive through hole 27b by a wiring pattern 24b; the signal output terminal 26c is connected to an electrical conductive through hole 27c by a wiring pattern 24c; and the power supply terminal 26d is connected to an electrical conductive through hole 27d by a wiring pattern 24d. The through holes 27 penetrate from the bottom surface f1 of the housing portion 21 to a plane f4 of the cable connecting portion 25 on the opposite side of the bottom surface f1.

The cable connecting portion 25 is formed by cutting out the proximal end side of the distal end frame 20, and includes a plane f4 and a plane f5. The plane f5 is provided with cable connection electrodes 28 for connecting the cable 40. A cable connection electrode 28a is connected to the electrical conductive through hole 27a by a wiring pattern 29a; a cable connection electrode 28b is connected to the electrical conductive through hole 27b by a wiring pattern 29b; a cable connection electrode 28c is connected to the electrical conductive through hole 27c by a wiring pattern 29c; and a cable connection electrode 28d is connected to the electrical conductive through hole 27d by a wiring pattern 29d. The cable 40 is in a state where an insulating jacket 42 on the distal end side is removed to expose a core wire 41, and the exposed core wire 41 is connected to the cable connection electrode 28 by an electrical conductive material such as solder (not illustrated).

Furthermore, the cable connection electrode 28 and the core wire 41, and a wiring pattern 29 and the upper portion of the through hole 27 on the f4 surface side are covered with an insulating material such as an underfill material.

The endoscope distal end structure 100 has a configuration in which the imager 30 and the cable 40 are located in a projection plane of the distal end frame 20 in the optical axis direction in a state where the imager 30 is housed in the distal end frame 20 and the cable 40 is connected to the cable connecting portion 25. This configuration makes it possible to suppress an enlargement in diameter of the endoscope distal end structure 100.

The outer frame 10 has a hollow cylindrical shape with a proximal end side open. On a surface on the distal end side, an aperture 11, an aperture 12, and an aperture 13 are provided at positions respectively corresponding to the imager 30, the channel insertion hole 22, and the light guide insertion hole 23.

As described above, the ground terminal 26a is connected to the cable connection electrode 28a by the wiring pattern 24a, the through hole 27a, and the wiring pattern 29a; the communication terminal 26b is connected to the cable connection electrode 28b by the wiring pattern 24b, the through hole 27b, and the wiring pattern 29b; the signal output terminal 26c is connected to the cable connection electrode 28c by the wiring pattern 24c, the through hole 27c, and the wiring pattern 29c; and the power supply terminal 26d is connected to the cable connection electrode 28d by the wiring pattern 24d, the through hole 27d, and the wiring pattern 29d.

In the present embodiment, the connection terminals 26 are each connected to the cable connection electrodes 28 by the through holes 27 penetrating from the bottom surface f1 of the housing portion 21 to the plane f4 of the cable connecting portion 25 on the opposite side of the bottom surface f1, making it possible to reduce the distance of signal transmission as compared with the case where the wiring patterns are formed on the outer periphery of the distal end frame 20, leading to reduction of the influence of noise or the like.

The side surface f6 of the distal end frame 20 includes an electrical conductive pattern 51 connecting the cable connection electrode 28a connected to the ground terminal 26a, to the ground pattern 50. In cases where a distal end member formed of resin having no electrical conductivity is adopted in the endoscope distal end structure, application of static electricity or a leakage current would destroy the image sensor due to a failure in giving electrical conduction to the ground of the operating unit 7 or the like by the electrical conductive member. In the present embodiment, the ground pattern 50 is formed on the bottom surface f1, the first side surface f2, and the second side surface f3 of the housing portion 21, and the electrical conductive pattern 51 on the side surface f6 of the distal end frame 20 connects the cable connection electrode 28a connected to the ground terminal 26a, to the ground pattern 50, and these passages are not covered with an insulating material such as an underfill material. In application of static electricity or the like to the endoscope distal end structure 100, the path including the ground pattern 50, the electrical conductive pattern 51, the cable connection electrode 28a, and a cable 40a has a lower impedance than the through hole 27a connected to the ground terminal 26a of the image sensor, which allows the current to flow easily. This makes it possible to give electrical conduction to the ground of the operating unit 7 or the like by the path of the cable 40a or the like, leading to prevention of destruction of the image sensor.

In the present embodiment, the ground patterns 50 are formed on the bottom surface f1, the first side surface f2, and the second side surface f3 of the housing portion 21. The disclosure, however, is not limited thereto, and the ground patterns may be formed only on the entire surfaces of the first side surface f2 and the second side surface f3, or the ground patterns 50 may be formed on a part of the distal end side of the first side surface f2 and the second side surface f3 as long as the patterns can provide sufficient electrical conduction with the electrical conductive patterns 51. Note that it is preferable to make the area of the ground pattern 50 larger in order to lower the impedance.

Furthermore, in the present embodiment, the inside of the subject is illuminated by the light guide. However, in a case where illumination is provided by a light emitting diode (LED), the LED mounting region can also have a configuration similar to the housing portion in order to prevent the influence of static electricity or the like on the LED. For example, the LED mounting region can be formed with a bottom surface which is orthogonal to the optical axis of the imager 30 and on which a connection terminal connected to a terminal of the LED is formed together with a first side surface and a second side surface which are continuous to each other in parallel to the optical axis and on which a ground pattern is formed. In addition, by connecting the connection terminal to the cable connection electrode via an electrical conductive through hole, and by forming an electrical conductive pattern on a side surface of the distal end frame so as to connect the cable connection electrode connected to the ground terminal among the connection terminals, to the ground pattern, it is possible to prevent destruction of the LED due to static electricity or the like.

Figure 4:
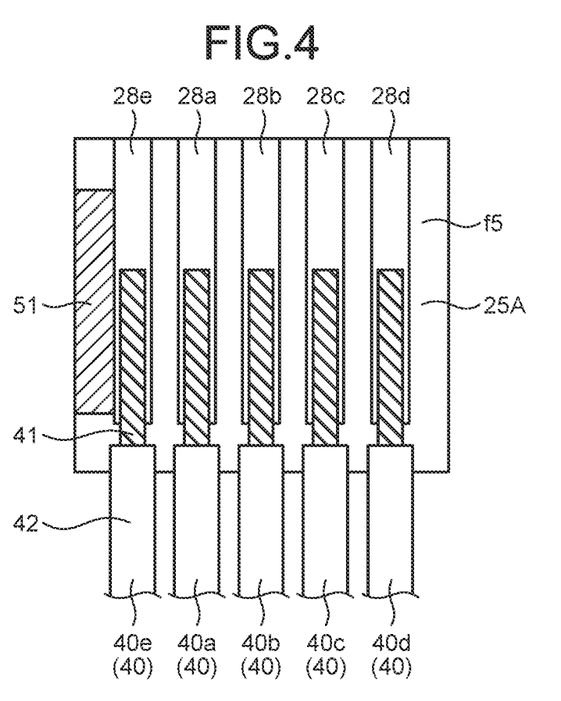
FIG. 4 is a view illustrating a cable connecting portion of a distal end frame according to a first modification of the embodiment of the disclosure.

Furthermore, although the above embodiment has a configuration in which the cable connection electrode 28a connected to the ground terminal 26a of the image sensor is connected with the ground pattern 50 by using the electrical conductive pattern 51, it is also allowable to provide a cable connection electrode and a cable dedicated to static electricity. FIG. 4 is a view illustrating a cable connecting portion 25A of a distal end frame according to a first modification of the embodiment of the disclosure.

The cable connecting portion 25A is provided with a cable connection electrode 28e dedicated to static electricity in addition to the cable connection electrodes 28a to 28d, and is connected to the ground pattern 50 by the electrical conductive pattern 51. The cable connection electrode 28e is connected with a cable 40e dedicated to static electricity. When static electricity or the like is applied, it is possible to achieve electrical conduction to the ground of the operating unit 7 or the like by the ground pattern 50, the electrical conductive pattern 51, the cable connection electrode 28e, and the cable 40e. This makes it possible to further reduce the influence of static electricity or the like on the image sensor.

Figure 5:
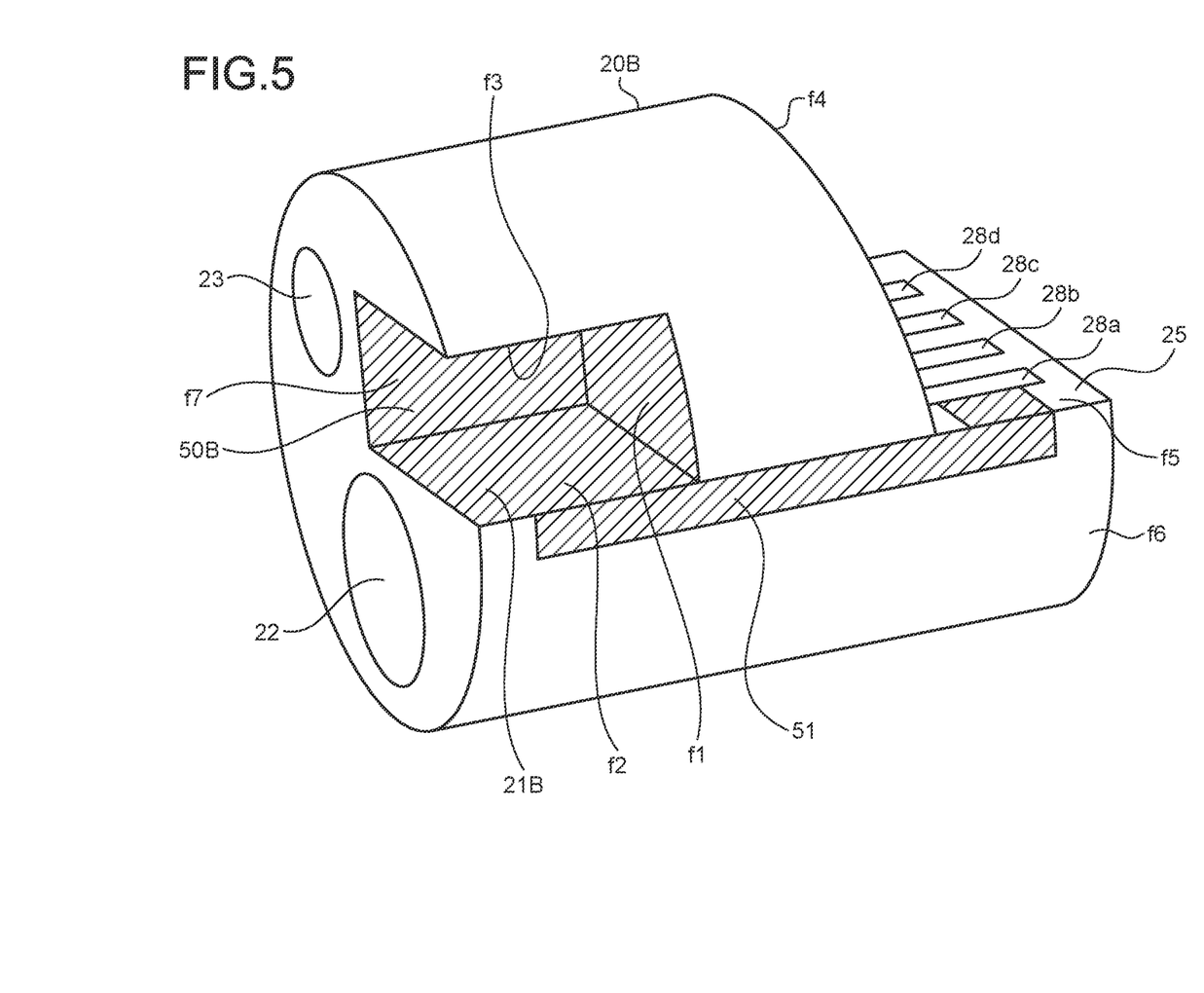
FIG. 5 is a perspective view of a distal end frame according to a second modification of the embodiment of the disclosure.

Furthermore, the shape of housing portion 21 is not limited to the shape described in the first embodiment. FIG. 5 is a perspective view of a distal end frame 20B according to a second modification of the embodiment of the disclosure. Note that FIG. 5 omits illustration of the connection terminals 26, wiring patterns 24, and the through holes 27.

A housing portion 21B includes: a bottom surface f1 which is orthogonal to the optical axis of the imager 30 and on which a connection terminal 26 connected to a terminal of the image sensor is formed; and a first side surface f2, a third side surface f7, and a second side surface f3 which are continuous to each other in parallel to the optical axis. The third side surface f7 is continuous to the first side surface and the second side surface. There is provided a ground pattern 50B formed on the first side surface f2, the third side surface f7, and the second side surface f3, and around the connection terminal 26, the wiring pattern 24, and the through hole 27 (not illustrated) on the bottom surface f1.

Also in the distal end frame 20B according to the second modification, similarly to the first embodiment, in a case where static electricity or the like is applied to the endoscope distal end structure 100, it is possible to achieve electrical conduction to the ground of the operating unit 7 or the like by the ground pattern 50B, the electrical conductive pattern 51, the cable connection electrode 28a, and the cable 40a, leading to the prevention of destruction of the image sensor.

Although the embodiment uses a structure in which the distal end frame 20 is covered with the outer frame 10, the outer frame 10 would not have to be used.

The endoscope distal end structure of the disclosure is useful for an endoscope system that is required to reduce the diameter and the cost.

According to the disclosure, it is possible to obtain an endoscope distal end structure formed of a resin member and capable of preventing destruction of an imager due to static electricity or the like.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope distal end structure comprising:
   an image sensor configured to capture an object image,
   a distal end frame comprising:
      a housing provided on a distal end side of the distal end frame, the housing being configured to house the image sensor, the housing comprising:
         a bottom surface disposed proximally relative to the image sensor, the bottom surface having connection terminals connected to the image sensor; and
         at least one first side surface extending distally from the bottom surface, a ground pattern being formed on the at least one first side surface;
      a cable connecting portion provided on a proximal end side of the distal end frame, the cable connecting portion comprising at least one surface, the at least one surface including a cable connection electrode corresponding to each of the connection electrodes, each of the connection electrodes being configured for connection to a cable,
   a through hole having electrical conductivity, the through hole penetrating proximally from the bottom surface to the cable connecting portion, and
   an electrical conductive pattern connecting one of the cable connection electrodes to a ground terminal among the connection terminals.

2. The endoscope distal end structure according to claim 1, wherein the ground pattern is arranged around the connection terminals, the through hole, and a wiring pattern connecting the connection terminal and the through hole.

3. The endoscope distal end structure according to claim 1, wherein
   the at least one first side surface comprises a first side surface, a second side surface and a third side surface each being parallel to an optical axis of the image sensor;
   the second side surface is continuous to the first side surface and the third side surface is continuous the second side surface and
   the first side surface, the second side surface and the third side surface have a ground pattern arranged thereon.

4. The endoscope distal end structure according to claim 3, further comprising an outer frame formed of a material having no electrical conductivity, the outer frame being configured to cover the distal end frame.

5. The endoscope distal end structure according to claim 1, wherein
the ground terminal comprises a first ground terminal connected to the image sensor and a second ground terminal for static electricity, and
the electrical conductive pattern is connected to the second ground terminal for static electricity.

6. An endoscope comprising the endoscope distal end structure according to claim 1.

7. The endoscope distal end structure according to claim 1, wherein the at least one surface of the cable connecting portion comprises a first surface and a second surface, the first surface is disposed proximally on an opposite side of the bottom surface, the second surface extends proximally from the first surface and includes the cable connection electrode.

8. The endoscope distal end structure according to claim 7, wherein the through hole penetrates from the bottom surface of the housing to the first surface of the cable connecting portion.

9. The endoscope distal end structure according to claim 1, wherein the electrical conductive pattern is arranged on an exterior surface of the distal end frame.

10. The endoscope distal end structure according to claim 1, wherein the ground pattern is formed on the bottom surface.

11. The endoscope distal end structure according to claim 1, wherein the distal end frame is a molded interconnect device.

12. The endoscope distal end structure according to claim 1, wherein a path including the ground pattern, the electrical conductive pattern, the cable connection electrode and the cable has an impedance lower than an impedance of the through hole connected to the ground terminal.

13. The endoscope distal end structure according to claim 1, further comprising an outer frame having no electrical conductivity, the outer frame being configured to cover an exterior of the distal end frame.

* * * * *